(12) United States Patent
Minobe

(10) Patent No.: US 11,592,372 B2
(45) Date of Patent: Feb. 28, 2023

(54) URINE TESTING APPARATUS AND URINE TESTING METHOD

(71) Applicant: Yukashikado Inc., Tokyo (JP)

(72) Inventor: Shinya Minobe, Tokyo (JP)

(73) Assignee: YUKASHIKADO INC., Tokyo (JP)

( * ) Notice: Subject to any disclaimer, the term of this patent is extended or adjusted under 35 U.S.C. 154(b) by 815 days.

(21) Appl. No.: 16/471,102

(22) PCT Filed: Dec. 19, 2017

(86) PCT No.: PCT/JP2017/045614
§ 371 (c)(1),
(2) Date: Jun. 19, 2019

(87) PCT Pub. No.: WO2018/117129
PCT Pub. Date: Jun. 28, 2018

(65) Prior Publication Data
US 2019/0331562 A1 Oct. 31, 2019

(30) Foreign Application Priority Data
Dec. 19, 2016 (JP) .............................. JP2016245880

(51) Int. Cl.
*G01N 1/38* (2006.01)
*C12Q 1/04* (2006.01)
(Continued)

(52) U.S. Cl.
CPC ................. *G01N 1/38* (2013.01); *C12Q 1/04* (2013.01); *G01N 1/10* (2013.01); *G01N 30/06* (2013.01);
(Continued)

(58) Field of Classification Search
CPC ............ G01N 1/38; G01N 1/10; G01N 30/06; G01N 33/82; G01N 2030/027;
(Continued)

(56) References Cited

U.S. PATENT DOCUMENTS 4,300,905 A 11/1981 Bleisteiner et al.
4,921,807 A 5/1990 Pak
(Continued)

FOREIGN PATENT DOCUMENTS

AU 2008276701 A 7/2008
CA 2806670 A1 2/2012
(Continued)

OTHER PUBLICATIONS

Extended European Search Report issued in corresponding EP Patent Application No. 17883837.1 dated Aug. 31, 2020.
(Continued)

*Primary Examiner* — Jennifer Wecker
*Assistant Examiner* — Michael Paul Shimek
(74) *Attorney, Agent, or Firm* — Morgan, Lewis & Bockius LLP

(57) ABSTRACT

There are provided a urine testing apparatus and a urine testing method which can stabilize urine vitamins for several days and improve testing accuracy and convenience of a urine collection test of a subject. According to this urine testing apparatus, the inner wall surface of a urine collection storage container is coated with an aqueous citric acid solution or the like as a urine stabilizer. Alternatively, a dried or freeze-dried aqueous citric acid solution or the like as the urine stabilizer is stored in the urine collection storage container. On the other hand, according to the urine testing method of this invention, the aqueous citric acid solution or the like as the urine stabilizer is added to the collected urine sample, the vitamin concentration of at least 7 days after urine collection is stabilized to stabilize each urine vitamin for several days, thereby improving the convenience of the urine collection test of the subject. In particular, the urine concentrations of vitamins B can be stabilized to accurately test the nutrients lacking in the body of the subject.

20 Claims, 11 Drawing Sheets

(51) Int. Cl.
  *G01N 1/10*   (2006.01)
  *G01N 30/06*  (2006.01)
  *G01N 33/82*  (2006.01)
  *G01N 30/02*  (2006.01)

(52) U.S. Cl.
  CPC ....... *G01N 33/82* (2013.01); *G01N 2030/027* (2013.01)

(58) Field of Classification Search
  CPC ............. G01N 33/48778; G01N 33/84; G01N 33/493; C12Q 1/04
  See application file for complete search history.

(56) References Cited

U.S. PATENT DOCUMENTS

| | | |
|---|---|---|
| 6,261,844 B1 | 7/2001 | Smith et al. |
| 2003/0087330 A1 | 5/2003 | Glagau et al. |
| 2007/0134740 A1 | 6/2007 | Brusilovsky et al. |
| 2009/0157328 A1 | 6/2009 | Mann et al. |
| 2010/0233738 A1 | 9/2010 | Hara et al. |

FOREIGN PATENT DOCUMENTS

| | | | |
|---|---|---|---|
| CN | 101084944 A | | 12/2007 |
| CN | 101427673 A | | 5/2009 |
| EP | 0811844 A1 | | 10/1997 |
| EP | 0949507 A1 | | 10/1999 |
| EP | 1 204 324 | | 5/2002 |
| JP | S 53-48796 A | | 5/1978 |
| JP | 6-213885 | | 8/1994 |
| JP | 7-294519 | | 11/1995 |
| JP | 09-196909 | | 7/1997 |
| JP | 0811844 A1 | * | 12/1997 |
| JP | 10-282095 | | 10/1998 |
| JP | 2000-241424 | | 9/2000 |
| JP | 2000241424 A | * | 9/2000 |
| JP | 2003-52565 A | | 12/2000 |
| JP | 2003-505479 | | 2/2003 |
| JP | 2010-230618 | | 10/2010 |
| WO | WO 80/013 89 A | | 7/1980 |
| WO | WO 98/29745 | | 7/1998 |

OTHER PUBLICATIONS

Corrected European Search Report issued in corresponding EP Application No. 17883837.1 dated Feb. 24, 2021, 9 pages.
Notification to Grant Patent Right for Invention, including English translation, issued in corresponding CN Application No. 201780078874.0, dated Aug. 5, 2020, 7 pages.
Cuhadar et al., "The effect of storage time and freeze-thaw cycles on the stability of serum samples", Biochemia Medica, vol. 23(1):70-7, 2013.
English translation of International Search Report for International Application No. PCT/JP2017/045614, dated Mar. 27, 2018, 4 pages.
Office Action issued in corresponding European Patent Application No. 17883837.1 dated Jan. 13, 2023.

* cited by examiner

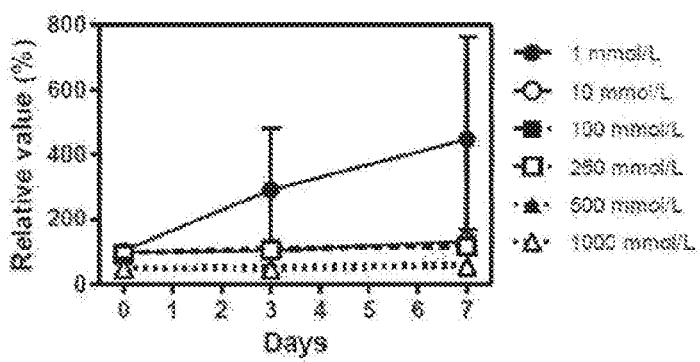
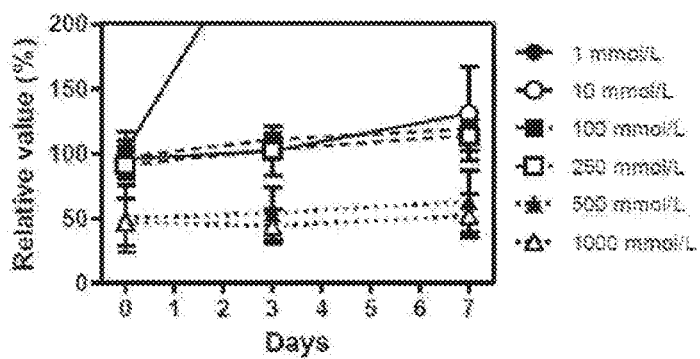
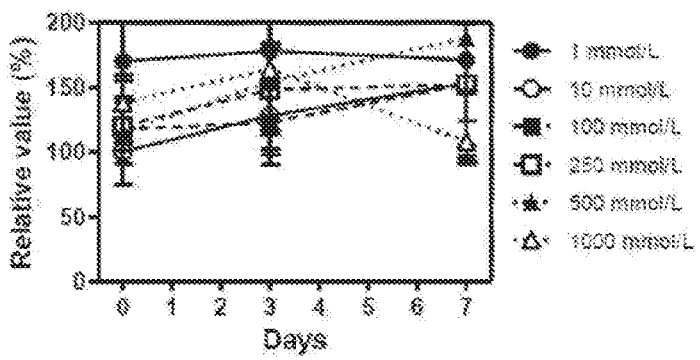
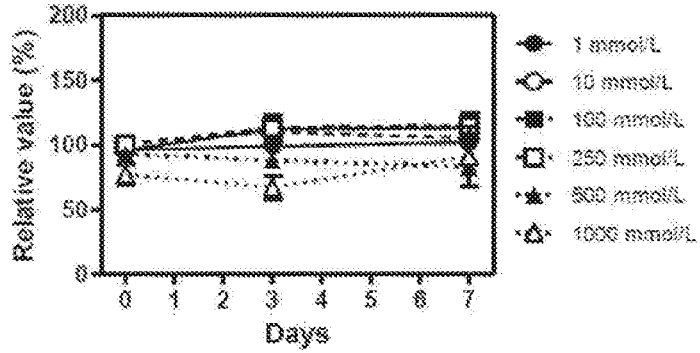
F I G. 8

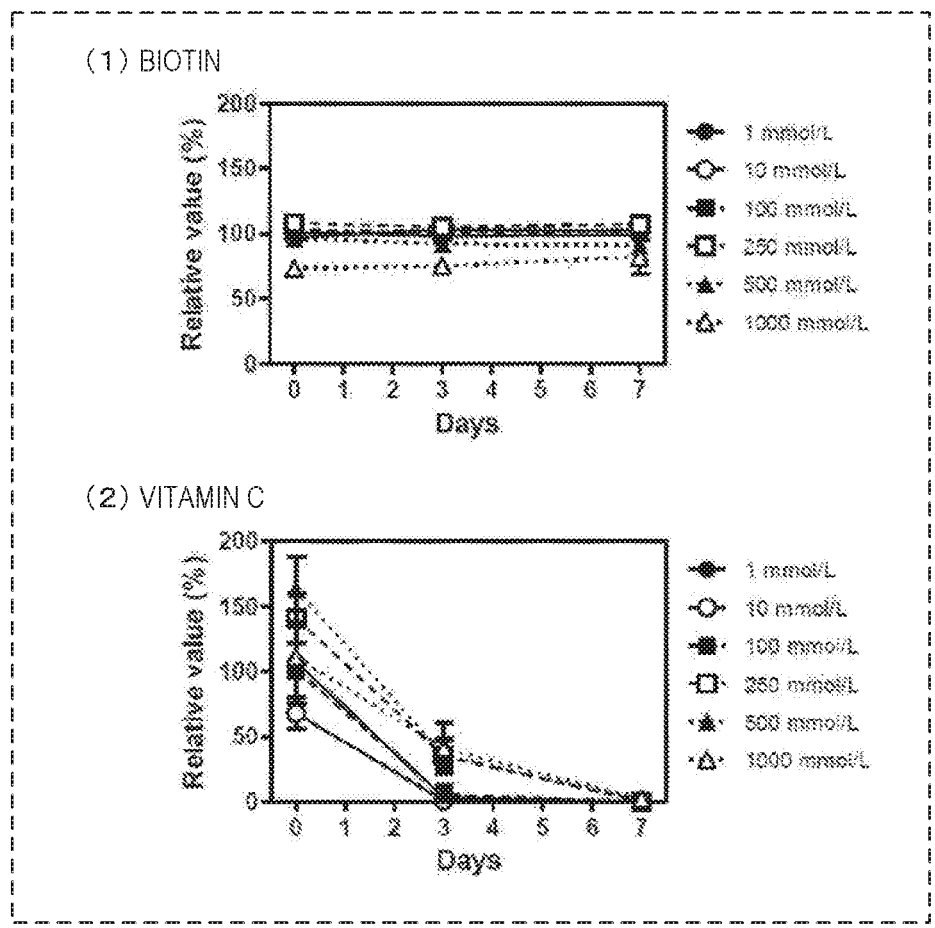
F I G. 10

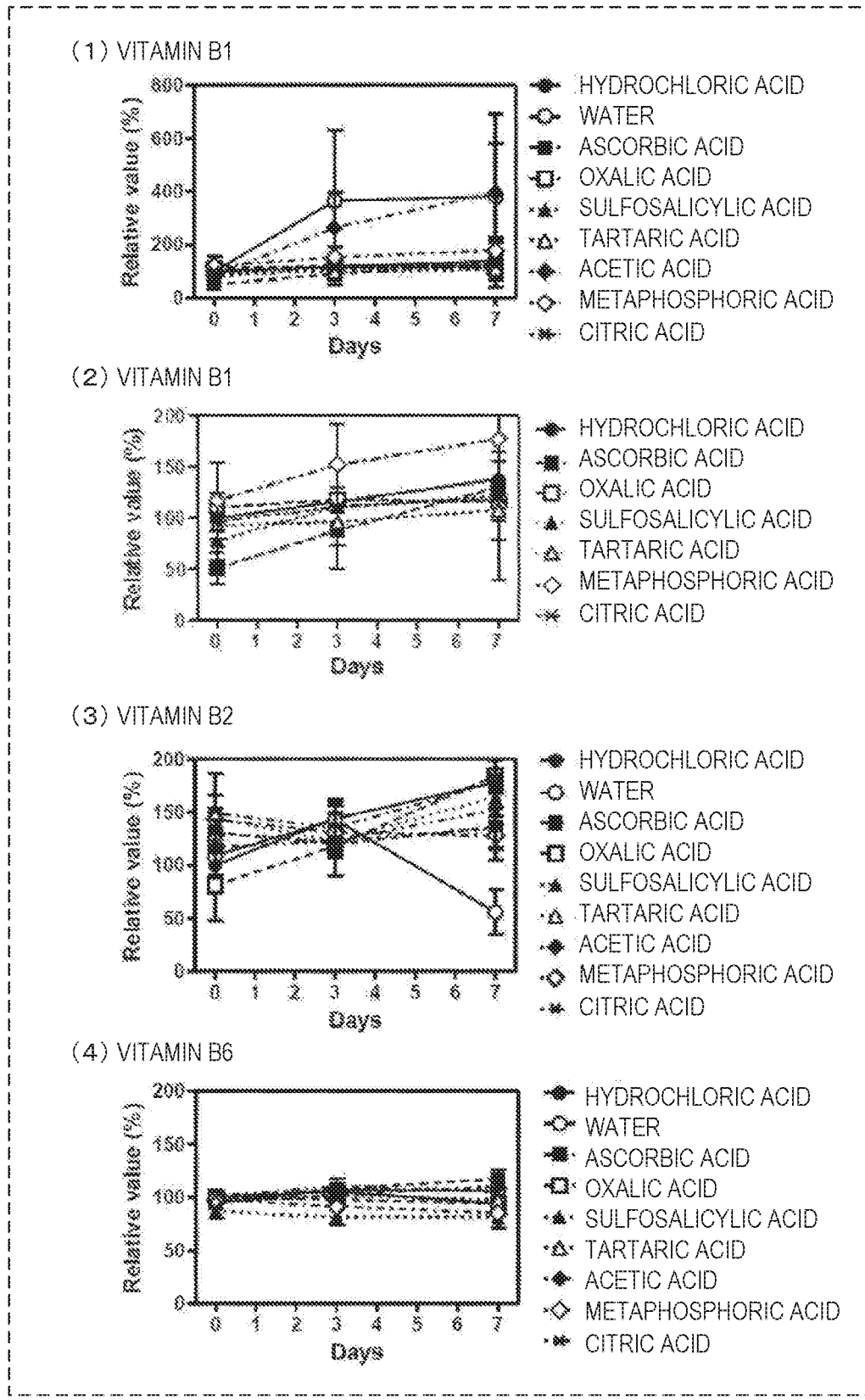
F I G. 11

URINE TESTING APPARATUS AND URINE TESTING METHOD

CROSS-REFERENCE TO RELATED APPLICATIONS

This application is the national stage entry of International Patent Application No. PCT/JP2017/045614, filed Dec. 19, 2017, which claims the benefit of priority from Japanese patent application No. 2016-245880, filed on Dec. 19, 2016, the disclosure of which are incorporated herein in its entirety by reference.

TECHNICAL FIELD

The present disclosure relates to a urine testing apparatus and a urine testing method using spot urine.

BACKGROUND

Conventionally, many urine tests have been conducted in hospitals and clinical laboratories. Most of these urine tests use 24-hour urine. In order to store 24-hour urine, it takes time and requires a high cost, resulting in cumbersome operations.

In order to solve this problem, there is known a measurement method of calculating the daily excretion amount of urine components as the total amount of components contained in daily urine from the urine components of spot urine samples collected a plurality of times (see patent literature 1).

According to the measurement method disclosed in patent literature 1, urine collection is easy and the urine components can be measured without storing 24-hour urine. However, in order to measure the urine components, each urine sample must be acidified to stabilize the urine components. The above problem cannot be solved even using the measurement method disclosed in patent literature 1.

When using 24-hour urine as a specimen, hydrochloric acid has generally been used as an additive for acidifying urine to stabilize the urine components. However, hydrochloric acid is a deleterious substance, and a problem is posed in viewpoint of safety and management facilitation.

CITATION LIST

Patent Literature

Patent literature 1: Japanese Patent Laid-Open No. 2010-230618

SUMMARY OF THE INVENTION

Technical Problem

The present invention provides a urine testing apparatus and a urine testing method that can stabilize urine vitamins and urine glucose for several days and improve testing accuracy and convenience of a urine test for a subject.

Solution to Problem

One example aspect of the present invention provides a urine testing apparatus characterized in that an agent obtained by drying or freeze-drying an aqueous solution containing a material selected from the group consisting of citric acid, oxalic acid, tartaric acid, ascorbic acid, and a combination thereof as a urine stabilizer is stored in a urine collection storage container.

According to the urine testing apparatus of the present invention, the urine vitamins can be stabilized for several days, and convenience of a urine collection test of a subject can be improved. The urine vitamins are vitamins B, and the examples of the vitamins B are six vitamins of vitamin B1, vitamin B2, vitamin B6, niacin, pantothenic acid, folate, and biotin. The vitamins B are nutrients indispensably required to create animal energy. These nutrients are known to act on metabolism of carbohydrates, fats, and proteins and associate with various metabolisms while maintaining the cooperation with the nutrients. By testing the urine concentrations of the vitamins B, a lack of the nutrients in the body of the subject can become obvious.

The stabilizer to be stored can be a stabilizer obtained by drying or freeze-drying an aqueous solution used as a stabilizer, thereby improving handling convenience.

The testing item of a urine test using the urine testing apparatus according to the present invention is not limited to the vitamins B, but can be vitamin C, minerals, and proteins. Oxalic acid is contained as a stabilizer, thereby stabilizing vitamin C.

Another aspect of the present invention provides a urine testing apparatus characterized in that an inner wall of a urine collection storage container is coated with an aqueous solution containing a material selected from the group consisting of citric acid, oxalic acid, tartaric acid, ascorbic acid, and a combination thereof as a urine stabilizer in the urine collection storage container.

Similarly, the urine vitamins can be stabilized for several days, and the convenience of a urine collection test of a subject can be improved. In particular, by testing the urine concentrations of the vitamins B, a lack of the nutrients in the body of the subject can become obvious.

Still other aspect of the present invention provides a urine testing apparatus characterized by comprising a container filled with an aqueous solution containing a material selected from the group consisting of citric acid, oxalic acid, tartaric acid, ascorbic acid, and a combination thereof as a urine stabilizer and a urine collection storage container.

By forming the stabilizer into a kit with a container different from the urine collection storage container, the convenience and efficiency of a test can be improved.

Still other aspect of the present invention provides a urine testing apparatus characterized by comprising a medium impregnated with an aqueous solution containing a material selected from the group consisting of citric acid, oxalic acid, tartaric acid, ascorbic acid, and a combination thereof as a urine stabilizer and a urine collection storage container.

An aqueous citric acid solution, an aqueous oxalic acid solution, or a mixture of the aqueous citric acid solution and the aqueous oxalic acid solution can preferably be used as the stabilizer for the urine testing apparatus according to the present invention.

In the urine testing apparatus according to the present invention, a citric acid concentration in a mixture of a stabilizer and urine is preferably 0.005 to 0.24 mol/L, and more preferably 0.01 to 0.1 mol/L, thereby sufficiently enhancing the effect of the stabilizer.

A stabilizer of about 1 mL is used.

A urine testing method according to the present invention will be described below.

Still other aspect of the present invention provides a urine testing method comprising adding, to collected urine, an aqueous solution obtained by mixing a material selected from the group consisting of citric acid, oxalic acid, tartaric acid, ascorbic acid, and a combination thereof as a urine stabilizer, thereby testing urine in which one of a urine vitamin concentration, a mineral concentration, and a protein concentration is stabilized for at least 7 days after urine collection. By stabilizing the urine vitamins for several days, the convenience of a urine collection test of a subject can be improved. In particular, by testing the urine concentrations of the vitamins B, lacking nutrients in the body of the subject can be accurately tested.

In this case, the vitamins are vitamins B that are vitamin B1, vitamin B2, vitamin B6, niacin, pantothenic acid, folate, and biotin. The minerals are sodium, calcium, potassium, phosphorus, and magnesium. Oxalic acid is contained in the stabilizer to allow stabilization of vitamin C.

An aqueous citric acid solution or a mixture of the aqueous citric acid solution and the aqueous oxalic acid solution can preferably be used as the stabilizer for the urine testing method according to the present invention. A mixing ratio of the aqueous citric acid solution to the aqueous oxalic acid solution preferably falls within the range of 3:7 to 7:3, and more preferably 4:6 to 6:4.

Still other aspect of the present invention provides the urine testing method wherein, by adding the above stabilizer, the urine vitamin concentration can be stabilized under a condition of 37° C. for at least 7 days after urine collection.

Still other aspect of the present invention provides a urine testing method comprising adding, to collected urine, an aqueous solution obtained by mixing a material selected from the group consisting of citric acid, oxalic acid, tartaric acid, ascorbic acid, and a combination thereof as a urine stabilizer, thereby testing urine in which a urine glucose concentration of at least 7 days after urine collection is stabilized. Normally, urine sugar (glucose: Glu) is said to become negative at room temperature. By using the urine testing method according to the present invention, the urine glucose concentration can be stabilized.

An aqueous citric acid solution or a mixture of the aqueous citric acid solution and the aqueous oxalic acid solution can preferably be used as the stabilizer for the urine testing method according to the present invention. A mixing ratio of the aqueous citric acid solution to the aqueous oxalic acid solution preferably falls within the range of 3:7 to 7:3, and more preferably 4:6 to 6:4.

Still other aspect of the present invention provides a urine testing method comprising adding, to collected urine, an aqueous solution containing one of oxalic acid and a combination of oxalic acid and one material selected from the group consisting of citric acid, tartaric acid, and ascorbic acid as a urine stabilizer, thereby testing urine in which a urine vitamin C concentration of at least 3 days after urine collection is stabilized.

That is, as for vitamin C not included in the above vitamins, the vitamin C concentration of 3 days after urine collection can be stabilized by using by aqueous solution containing one of oxalic acid and a combination of oxalic acid and one material selected from the group consisting of citric acid, tartaric acid, and ascorbic acid. This makes it possible to efficiently conduct a urine test.

According to each urine testing method of the present invention, urine is collected using the above urine testing apparatus according to the present invention, and urine in which the urine vitamin concentration of at least 7 days after the urine collection is stabilized is tested. According to the urine testing method of the present invention, urine is collected using the above urine testing apparatus of the present invention, and urine in which the urine mineral concentration of at least 7 days after the urine collection is stabilized is tested. According to the urine testing method of the present invention, urine is collected using the above urine testing apparatus of the present invention, and urine in which the urine protein concentration of at least 7 days after the urine collection is stabilized is tested. According to the urine testing method of the present invention, urine is collected using the above urine testing apparatus of the present invention, and urine in which the urine vitamin C concentration of at least 3 days after the urine collection is stabilized is tested. Urine is collected using the urine testing apparatus according to the present invention, convenience of a urine test of a subject can be improved. In particular, by testing the urine concentrations of the vitamins B, a lack of the nutrients in the body of the subject can be tested. According to the urine testing method of the present invention, urine is collected using the above urine testing apparatus of the present invention, and urine in which the urine glucose concentration of at least 7 days after the urine collection is stabilized is tested.

Advantageous Effects of Invention

According to the urine testing apparatus and the urine testing method of the present invention, urine vitamins, urine minerals, urine proteins, or urine glucose can be stabilized for several days. According to the effects of the present invention, the testing accuracy and the convenience of the urine collection test of the subject can be improved.

BRIEF DESCRIPTION OF DRAWINGS

FIG. 8 shows graphs 1 showing the stabilization of water-soluble vitamins in urine (Example 4);

FIG. 10 shows graphs 3 showing the stabilization of water-soluble vitamins in urine (Example 4);

FIG. 11 shows graphs 1 showing the stabilization of water-soluble vitamins in urine (Example 5);

DETAILED DESCRIPTION OF EMBODIMENTS

Example embodiments of the present invention will now be described in detail with reference to the drawings. It should be noted that the relative arrangement of the components, the numerical expressions and numerical values set forth in these example embodiments do not limit the scope of the present invention unless it is specifically stated otherwise.

A test conducted using a urine testing method of the present invention will be performed, for example, in the following manner.

Figure 1:
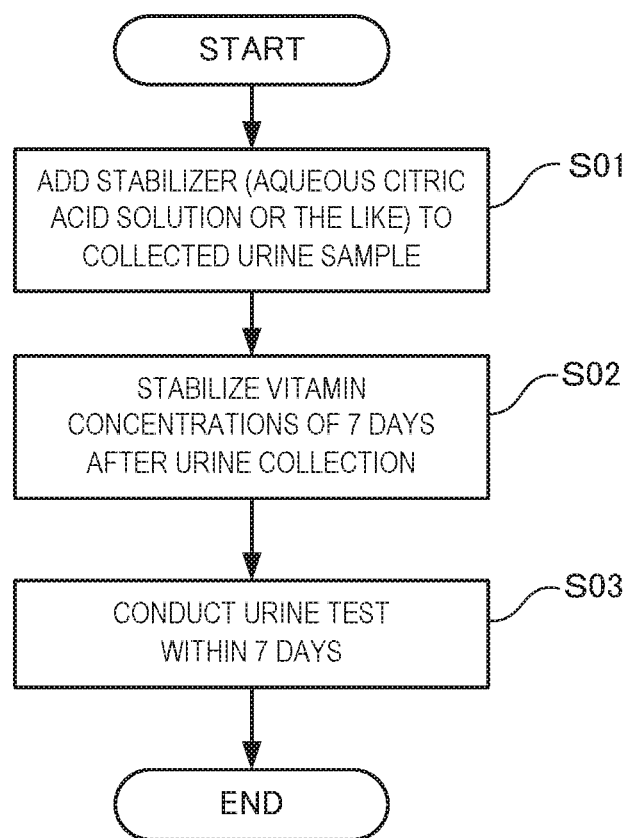
FIG. 1 is a flowchart showing a urine test.

FIG. 1 is a flowchart of a urine test. As shown in FIG. 1, a stabilizer (for example, an aqueous citric acid solution) is added to collected urine (S01). After the urine collection, the vitamin concentration of 7 days is stabilized (S02). A urine test is conducted within 7 days (S03).

When conducting the urine test, the urine vitamin concentration must be stabilized for several days. The types of materials effective as stabilizers and their concentrations are examined, and the examination results will be described in the following examples.

Example 1

The influences of the aqueous citric acid solution on the stability of the vitamins B in urine will be described with reference to FIGS. 2 and 3.

The vitamins B in urine are stabilized when they are stored in hydrochloric acid. As a stabilizer in place of hydrochloric acid, the aqueous citric acid solution is used and mixed with urine, and the urine is stored for 1 to 7 days. The changes in concentrations of the vitamins B added with the aqueous citric acid solution are shown in FIGS. 2 and 3.

Figure 2:
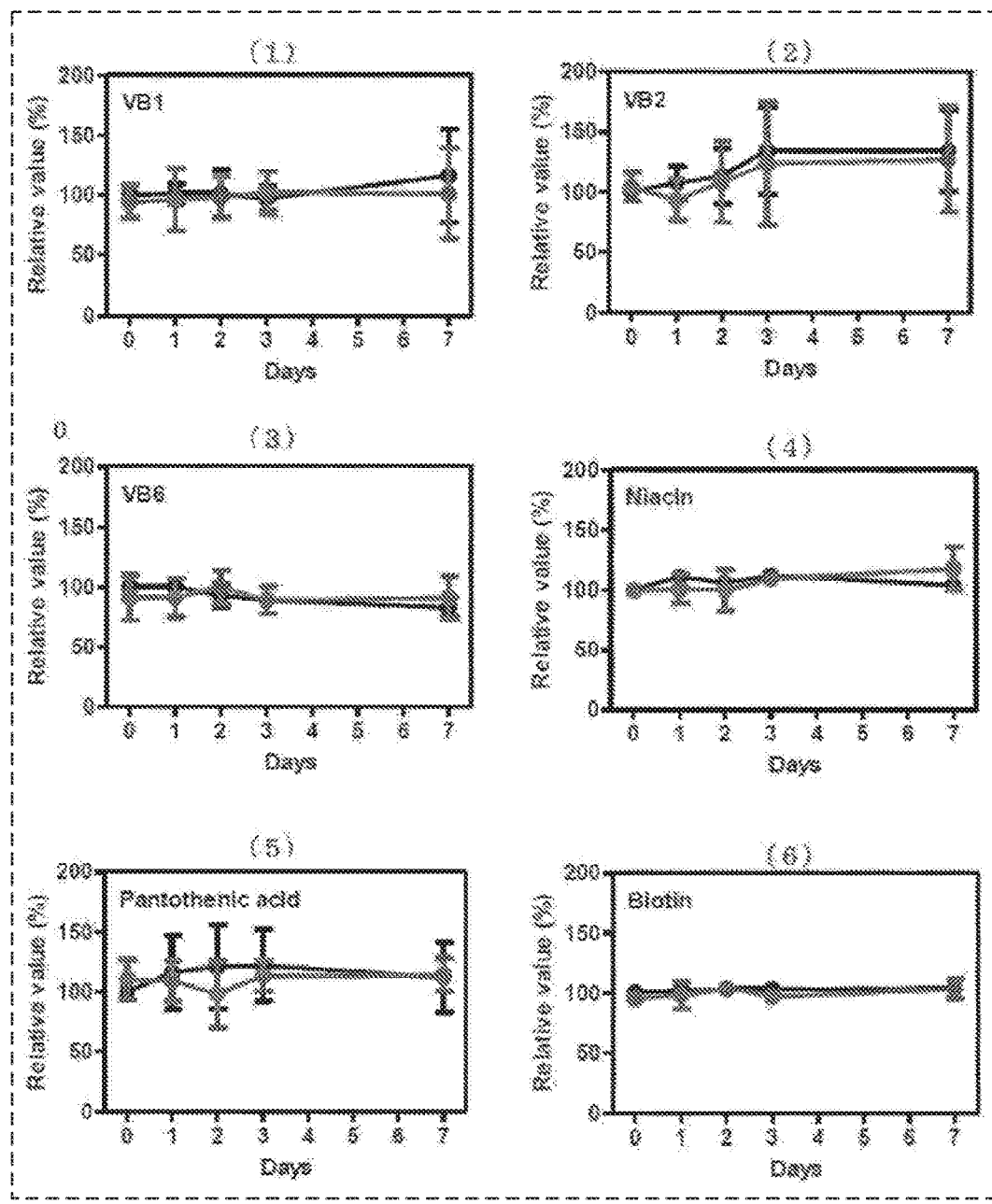
FIG. 2 shows graphs showing the stabilization of vitamins B in urine (Example 1)

(1) to (6) in FIG. 2 show changes in concentrations of vitamin B1, vitamin B2, vitamin B6, niacin, pantothenic acid, and biotin. FIG. 3 shows changes in concentrations of folate.

First, spot urine samples were collected from three healthy young adults. 9 mL of each spot urine sample was mixed with a 1 mL aqueous citric acid solution having a concentration of 1 mol/L. The samples were stored at 22° C. for 0, 1, 3, and 7 days. The concentrations of the vitamins B in the urine samples after the storage were measured. More specifically, the vitamin concentrations of vitamin B1, vitamin B2, and vitamin B6 were measured by a high performance liquid chromatography method (HPLC method) for thiamine, riboflavin, and vitamin B6 metabolite 4-pyridoxic acid, respectively. As for niacin, N1-methyl nicotinamide, N1-methyl-2-pyridone-5-carboxamide, and N1-methyl-4-pyridone-3-carboxamide as the niacin metabolites were measured by the HPLC method, and their total amount was defined as a measurement result. In addition, as for pantothenic acid, biotin, and folate, the respective vitamin concentrations were measured by a microbiological determination.

Note that as a comparative example, 9 mL of a spot urine sample and hydrochloric acid having a concentration of 1 mol/L were mixed, and vitamins B in the urine samples were measured after the samples were stored for 0, 1, 3, and 7 days at 22° C.

Figure 3:
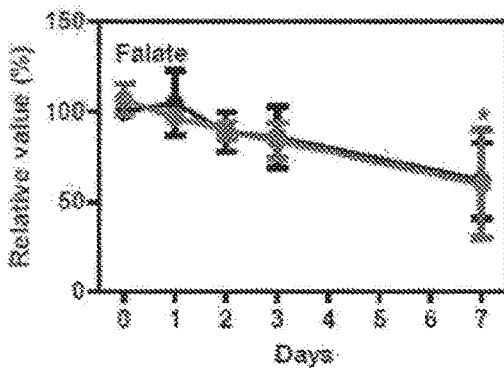
FIG. 3 is a graph showing the stabilization of folate (Example 1)

The graphs of changes in concentrations in FIGS. 2 and 3 show the relative values of the vitamins B in the urine samples each obtained by mixing the aqueous citric acid solution and the urine samples (to be referred to as a citric acid treatment hereinafter) using, as the reference, the concentrations of the vitamins B in the urine samples obtained by mixing hydrochloric acid and the urine samples immediately after collection (to be referred to as a hydrochloric acid treatment hereinafter). As shown in the graphs in (1) to (6) of FIG. 2, no significant changes due to the storage for 1 to 7 days were observed in the hydrochloric acid treatment and the citric acid treatment of vitamin B1 (VB1), vitamin B2 (VB2), vitamin B6 (VB6), niacin, pantothenic acid, and biotin. On the other hand, as shown in the graphs in FIG. 3, the urine folate concentrations of 7-day storage were reduced to about 60% in both the hydrochloric acid treatment and the citric acid treatment.

From the above results, it is found that the urine is treated by the citric acid treatment to allow 7-day stable storage of the vitamins B in the urine. It is obvious that citric acid can be used as a stabilizer in place of hydrochloric acid.

Example 2

The influences of a citric acid powder on the stability of the vitamins B in urine will be described with reference to FIGS. 4 and 5.

If an ordinary person handles a tube filled with a liquid, he/she may spill the liquid. In order to determine whether an aqueous citric acid solution in a tube is freeze-dried, and the vitamins B in urine can be stably stored even using this tube, the citric acid powder was mixed with collected urine samples, and the concentrations of the vitamins B after the 3-day storage were measured, as shown in FIGS. 4 and 5.

Figure 4:
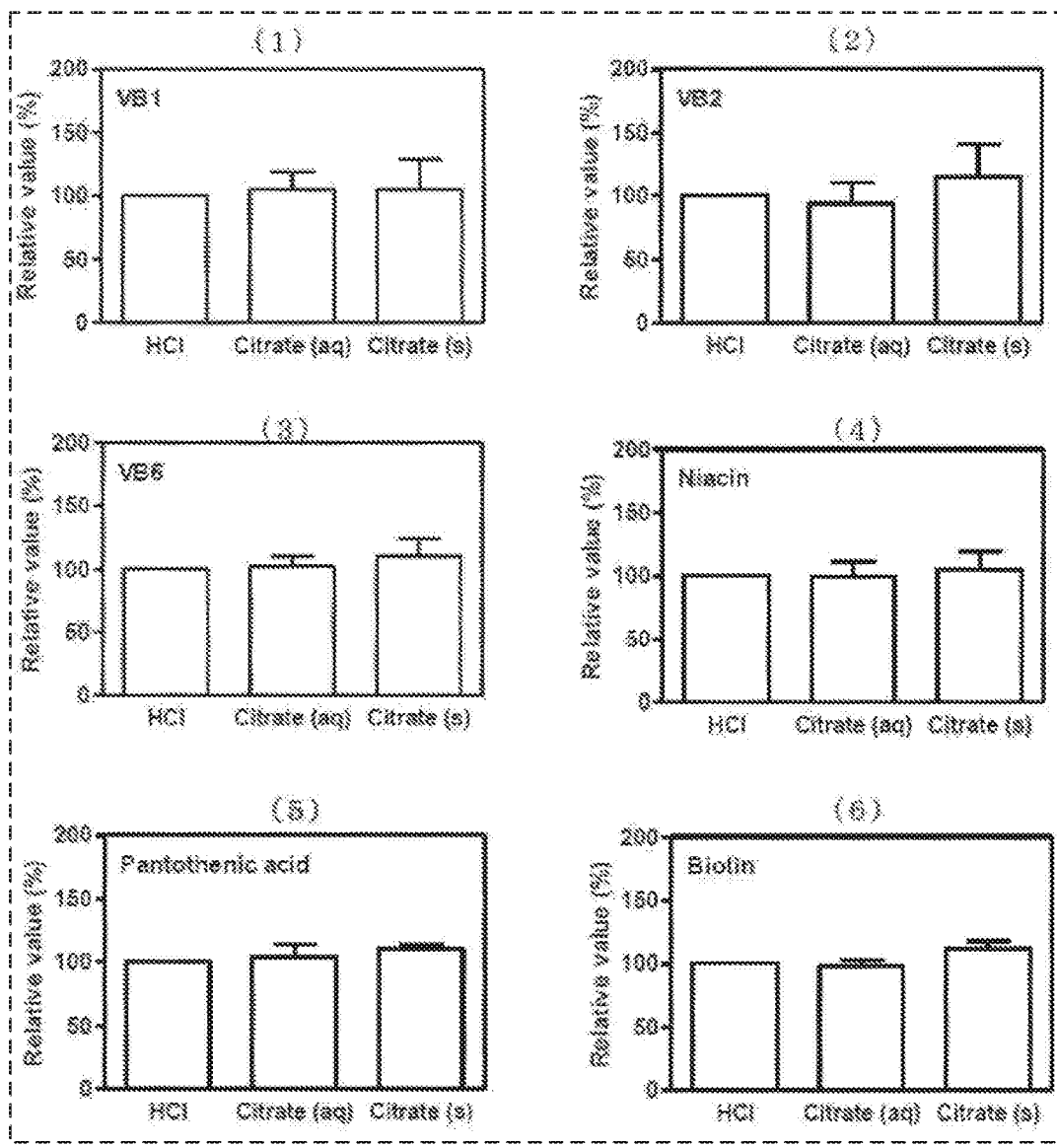
FIG. 4 shows graphs showing the stabilization of urine vitamins B (Example 2)

(1) to (6) in FIG. 4 show the concentrations of vitamin B1, vitamin B2, vitamin B6, niacin, pantothenic acid, and biotin when the urine samples were mixed with hydrochloric acid, the aqueous citric acid solution, or the citric acid powder. FIG. 5 shows the concentrations of folate when each urine sample was mixed with hydrochloric acid, the aqueous citric acid solution, or the citric acid powder.

A 1 mL aqueous citric acid solution having a concentration of 1 mol/L was poured into a 10 mL plastic tube, and the aqueous citric acid solution in the tube was freeze-dried. Spot urine samples were collected from three healthy young adults, and each spot urine sample of 9 mL was poured into a tube and was stored for 3 days at 22° C.

The vitamin concentrations were measured for the vitamins B in the urine samples after the storage. More specifically, the vitamin concentrations of vitamin B1, vitamin B2, and vitamin B6 were measured by the HPLC method for thiamine, riboflavin, and vitamin B6 metabolite 4-pyridoxic acid, respectively. As for niacin, N1-methyl nicotinamide, N1-methyl-2-pyridone-5-carboxamide, and N1-methyl-4-pyridone-3-carboxamide as the niacin metabolites were measured by the HPLC method, and their total amount was defined as a measurement result. In addition, as for pantothenic acid, biotin, and folate, the respective vitamin concentrations were measured by a microbiological determination.

Note that as a comparative example, 9 mL of a spot urine sample and an aqueous citric acid solution or hydrochloric acid having a concentration of 1 mol/L were mixed, and vitamins B in the urine samples were measured after the samples were stored for 3 days at 22° C.

Figure 5:
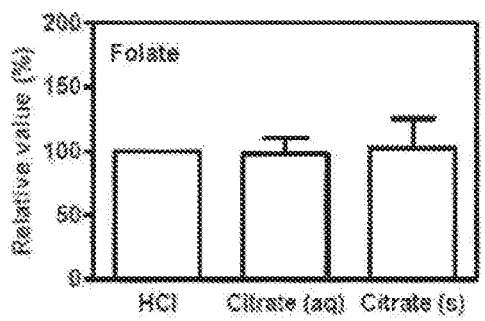
FIG. 5 is a graph showing the stabilization of folate (Example 2)

FIGS. 4 and 5 show the relative values of the vitamins B in urine treated with the aqueous citric acid solution or the freeze-dried citric acid using, as the reference, the vitamins B in urine of each person stored for 3 days after the hydrochloric acid treatment.

As shown in (1) to (6) of FIG. 4 and the graph of FIG. 5, the same values as in the hydrochloric acid treatment were exhibited in all the treatments with the aqueous citric acid solution or freeze-dried citric acid for all of vitamin B1 (VB1), vitamin B2 (VB2), vitamin B6 (VB6), niacin, pantothenic acid, biotin, and folate.

From the above results, it is found that the vitamins B in urine can be stably stored for 3 days using the tube in which the aqueous citric acid solution is freeze-dried.

Example 3

The settings of the reference values of excretion amounts of the vitamins B6 in spot urine samples corresponding to the reference values of the excretion amounts of the vitamins B in 24-hour urine samples will be described below with reference to FIGS. 6 and 7.

Figure 6:
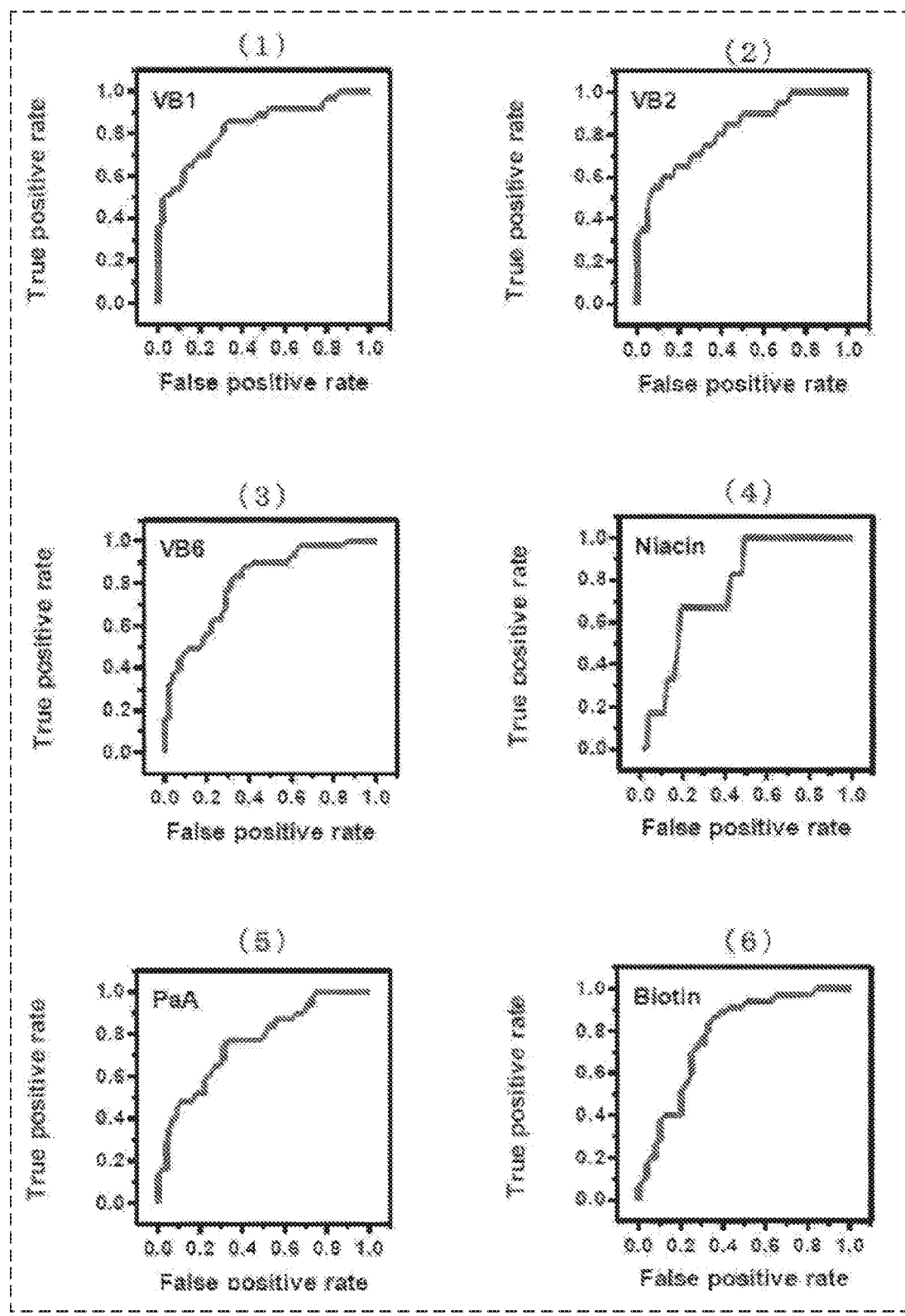
FIG. 6 shows ROC curves in excretion amounts of urine vitamins B.
Figure 7:
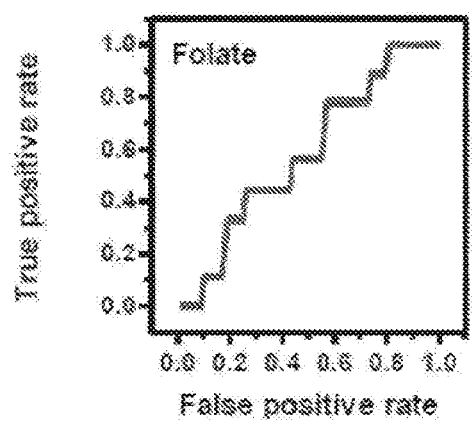
FIG. 7 shows an ROC curve in excretion amount of folate.

FIGS. 6 and 7 show receiver operating characteristic curves (ROC curves) in the excretion amounts of the vitamins B in each urine sample.

As the measurement method, data of 86 female students whose excretion amounts of the vitamins in the 24-hour urine samples and the spot urine samples were used. Using the ROC curves shown in FIGS. 6 and 7, the cutoff values of the excretion amounts in the spot urine samples which could clear the reference values of the respective vitamins in the 24-hour urine samples were decided.

As described above, the results obtained by deciding the cutoff values of the excretion amounts of the water-soluble vitamins in the spot urine samples, which can clear the reference values of the excretion amounts of the water-soluble vitamins in the 24-hour urine samples, are shown in Table 1 below.

TABLE 1

| Name of Vitamin | Cutoff Value (24-Hour Urine) | Cutoff Value (Spot Urine) | Sensitivity | Specificity | AUC |
| --- | --- | --- | --- | --- | --- |
| Vitamin B1 | 300 nmol/day | 260 nmol/g cre | 0.84 | 0.69 | 0.83 |
| Vitamin B2 | 200 nmol/day | 160 nmol/g cre | 0.65 | 0.82 | 0.81 |
| Vitamin B6 | 3.0 µmol/day | 3.0 µmol/g cre | 0.8 | 0.69 | 0.8 |
| Niacin | 50 µmol/day | 62 µmol/g cre | 0.67 | 0.81 | 0.76 |
| Pantothenic Acid | 10 µmol/day | 14.5 µmol/g cre | 0.77 | 0.67 | 0.76 |
| Biotin | 50 nmol/day | 80 nmol/g cre | 0.83 | 0.67 | 0.79 |
| Folate | 15 nmol/day | 16 nmol/g cre | 0.44 | 0.74 | 0.58 |

As shown in Table 1, as for sensitivity, 65% to 84% of the target persons whose excretion amounts in the 24-hour urine samples exceeded the reference values could be detected for the vitamins B except folate using the respective cutoff values. Since the specificity could be obtained by equation (1), the false positive rate which detected target persons having values less than the reference values was 10% to 33%.

Specificity=1−false positive rate    (1)

As shown in Table 1 above, the areas under the ROC curves (AUC) of the vitamins except folate were about 0.8 with intermediate accuracies of 0.7 to 0.9. However, as for folate, since there were only seven target persons out of the 86 target persons who exhibited excretion amounts in the 24-hour urine samples to be equal to or less than the reference values, the sensitivity was 0.44 lower than the other vitamins B. The AUC of folate was 0.58 which was classified in the low-accuracy range of 0.5 to 0.7.

Judging from the above results, the reference values of the spot urine samples decided in this example were obviously effective in easily evaluating the nutrient states of the six types of vitamins B except folate.

Example 4

An influence of a difference in citric acid concentration on the stability of the water-soluble vitamins in urine will be described with reference to FIG. 8.

Figure 9:
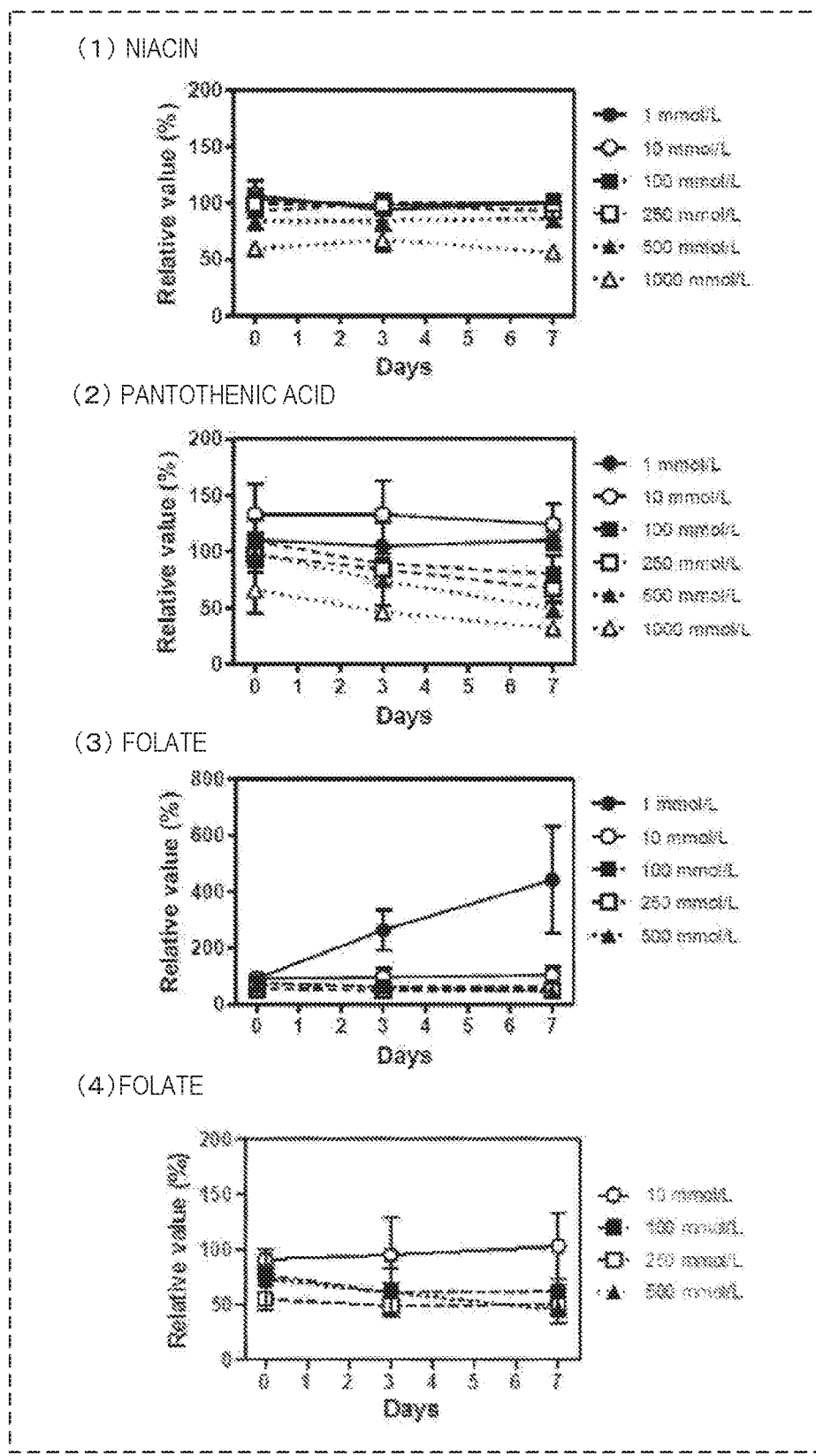
FIG. 9 shows graphs 2 showing the stabilization of water-soluble vitamins in urine (Example 4)

Each water-soluble vitamin in urine is stable when it is stored with citric acid having a concentration of 100 mmol/L. In order to clarify the citric acid concentration at which the stability function of citric acid is exhibited, each urine sample was mixed with an aqueous citric acid solution such that the final concentration of citric acid was set to 1 to 1,000 mmol/L, and the change in concentration of each vitamin after the storage for 0, 3, or 7 days was measured. The measurement results are shown in FIGS. 8 to 10. Note that the storage for 0 days indicates that the sample is freeze-dried immediately after mixing.

In FIG. 8, (1) and (2) indicate the concentration changes of vitamin B1, (3) indicates the concentration change of vitamin B2, and (4) indicates the concentration change of vitamin B6. In FIG. 9, (1) indicates the concentration change of niacin, (2) indicates the concentration change of pantothenic acid, and (3) and (4) indicate the concentration changes of folate. In FIG. 10, (1) indicates the concentration change of biotin, and (2) indicates the concentration change of vitamin C.

In this case, (1) and (2) in FIG. 8 and (3) and (4) in FIG. 9 are cases in which the scales in the ordinates are different.

Spot urine samples were collected from three healthy young adults. 9 mL of each of these spot urine samples were mixed with 1 mL aqueous citric acid solution having a concentration of 10 mmol/L to 10 mol/L, and the resultant samples were left still at 37° C. for 0, 3, and 7 days and freeze-dried. The final concentrations of citric acid were 1, 10, 100, 250, 500, and 1,000 mmol/L. Under these conditions, the concentrations of the water-soluble vitamins in the frozen urine samples were measured. More specifically, the vitamin concentrations of vitamin B1, vitamin B2, and vitamin B6 were measured by the HPLC method for thiamine, riboflavin, and vitamin B6 metabolite 4-pyridoxic acid, respectively. As for niacin, N1-methyl nicotinamide and N1-methyl-2-pyridone-5-carboxamide as the niacin metabolites were measured, and their total amount was defined as a measurement result. In addition, as for pantothenic acid, biotin, and folate, the respective vitamin concentrations were measured by a microbiological determination. As for vitamin C, a total amount of ascorbic acid, dehydroascorbic acid, 2,3-ketogulonic acid was measured by the HPLC method.

The graphs of the concentration changes in FIGS. 8 to 10 represent the relative values of the concentrations of the water-soluble vitamins treated with the aqueous citric acid solutions having the respective concentrations using, as the references, the water-soluble vitamins in the urine samples treated with hydrochloric acid immediate after urine collection. Note that each value in each graph is indicated by a relative value average±standard deviation (n=3 but n=2 for vitamin C) with each chlorine acid treated sample immediately after urine collection.

As shown in the graphs of (1) and (2) of FIG. 8, as for vitamin B1, large variations due to the 7-day storage were observed at the concentrations of 10 to 250 mmol/L. The urine thiamin concentration was increased twice or more by storage of 3 or more days after the treatment at the concentration of 1 mmol/L. The urine thiamin concentration was decreased to about 50% at a concentration of 500 mmol/L or more.

As shown in the graph of (3) of FIG. 8, as for vitamin B2, no large variation due to the storage up to the 3rd day could not be observed at the concentrations of 10 to 1,000 mmol/L. The urine riboflavin concentration was increased to about 1.5 times due to the 7-day storage. The urine riboflavin concentration was increased to 1.8 times after the water treatment at the concentration of 1 mmol/L.

As shown in the graph of (4) in FIG. 8, as for vitamin B6, no large variations due to the 7-day storage were observed at the respective concentrations.

As shown in the graph of (1) in FIG. 9, as for niacin, no large variation due to the 7-day storage was observed at the concentration of 500 mmol/L or less. The urine nicotinamide metabolite concentration was decreased to 60% to 70% at the concentration of 1,000 mmol/L.

As shown in the graph of (2) in FIG. 9, as for pantothenic acid, no large variation due to the 7-day storage was observed at the concentration of 100 mmol/L or less. The urine pantothenic acid concentration was decreased depending on the concentration of 250 mmol/L or more.

As shown in the graphs of (3) and (4) in FIG. 9, as for folate, no large variations due to the 7-day storage were observed at the concentration of 10 mmol/L. The urine folate concentration was decreased to about 60% at the concentration of 100 mmol/L due to the storage of 3 or more days. The urine folate concentration was decreased to about 50% at the concentration of 250 mmol/L or more. At the concentration of 1,000 mmol/L, the proliferation of bacteria was observed at the time of measurement, thereby disabling the measurement.

As shown in the graph of (1) in FIG. 10, as for biotin, no large variation due to the 7-day storage was observed at any concentration.

As shown in the graph of (2) in FIG. 10, as for vitamin C, a total urine ascorbic acid concentration was decreased to 30% or less due to the 3-day storage and was decreased to almost 0% due to the 7-day storage.

The summary of the influences of the differences in the concentrations of the aqueous citric acid solutions on the concentrations of the water-soluble vitamins in the urine samples is shown in Table 2 below. In Table 2, the average value of the relative values falling with the range of 75% to 150% using, as the reference, the value of the 0-day hydrochloric acid treatment is evaluated as ○, the average value falling within the range of 50% to 75% or 150% to 200% using, as the reference, the value of the 0-day hydrochloric acid treatment is evaluated as Δ, and the average value falling within the range of less than 50% or 200% or more using, as the reference, the value of the 0-day hydrochloric acid treatment is evaluated as x.

TABLE 2

| Final Concentration (mmol/L) | 0 Days | 3 Days | 7 Days | 0 Days | 3 Days | 7 Days | 0 Days | 3 Days | 7 Days | 0 Days | 3 Days | 7 Days |
|---|---|---|---|---|---|---|---|---|---|---|---|---|
| | Vitamin B1 | | | Vitamin B2 | | | Vitamin B6 | | | Niacin | | |
| 1 | ○ | X | X | Δ | Δ | Δ | ○ | ○ | ○ | ○ | ○ | ○ |
| 10 | ○ | ○ | ○ | ○ | ○ | Δ | ○ | ○ | ○ | ○ | ○ | ○ |
| 100 | ○ | ○ | ○ | ○ | ○ | Δ | ○ | ○ | ○ | ○ | ○ | ○ |
| 250 | ○ | ○ | ○ | ○ | ○ | Δ | ○ | ○ | ○ | ○ | ○ | ○ |
| 500 | Δ | Δ | Δ | ○ | Δ | Δ | ○ | ○ | ○ | ○ | ○ | ○ |
| 1000 | X | X | Δ | ○ | Δ | ○ | ○ | Δ | ○ | Δ | ○ | Δ |
| | Pantothenic Acid | | | Folate | | | Biotin | | | Vitamin C | | |
| 1 | ○ | ○ | ○ | ○ | X | X | ○ | ○ | ○ | ○ | X | X |
| 10 | ○ | ○ | ○ | ○ | ○ | ○ | ○ | ○ | ○ | Δ | X | X |
| 100 | ○ | ○ | ○ | ○ | Δ | Δ | ○ | ○ | ○ | ○ | X | X |
| 250 | ○ | ○ | ○ | Δ | X | Δ | ○ | ○ | ○ | ○ | X | X |
| 500 | ○ | Δ | X | Δ | Δ | X | ○ | ○ | ○ | ○ | X | X |
| 1000 | Δ | X | X | ... | ... | ... | Δ | ○ | ○ | ○ | X | X |

From the above results, it was found that the concentration of citric acid as an acid which exhibited the same stability as that of hydrochloric acid was the final concentration of 10 to 100 mmol/L for the seven water-soluble vitamins except vitamin C. It was found that the citric acid concentration of 250 mmol/L degraded the stability of folate, and the citric acid concentration of 500 mmol/L or more degraded the stability of vitamin B1, pantothenic acid, and folate.

Example 5

An influence of each kind of acidic solution on the stability of each water-soluble vitamin in urine will be described with reference to FIGS. 11 to 13.

The water-soluble vitamins in urine samples are stable when they are stored with hydrochloric acid. In Examples 1 to 4, experiments were conducted using the aqueous citric acid solutions. In this example, an experiment was conducted to consider any stabilizer candidate instead of hydrochloric acid except citric acid. As the stabilizer candidate instead of hydrochloric acid, each kind of acidic solution was mixed with each urine sample, and changes in vitamin concentrations after 0-, 3-, and 7-day storages were measured. The results are shown in FIGS. 11 to 13. Note that data for hydrochloric acid and citric acid are shown for comparison.

(1) and (2) in FIG. 11 indicate the changes in concentrations of vitamin B1, (3) indicates the change in concentration of vitamin B2, and (4) indicates the change in concentration of vitamin B6. (1) in FIG. 12 indicates the change in concentration of niacin, (2) indicates the change in concentration of pantothenic acid, and (3) and (4) indicate changes in concentrations of folate. (1) in FIG. 13 indicates the change in concentration of biotin, and (2) indicates the change in concentration of vitamin C.

Figure 12:
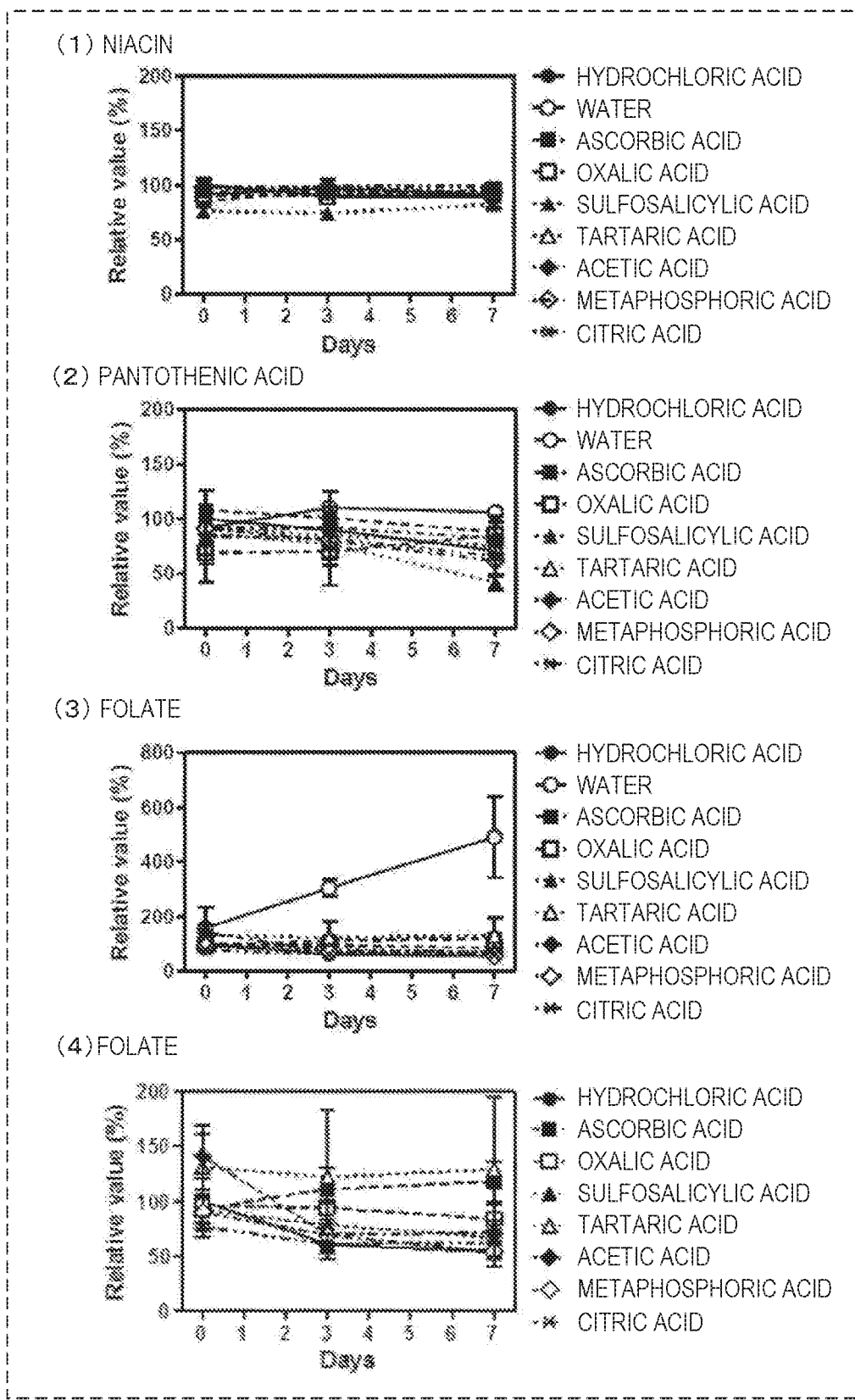
FIG. 12 shows graphs 2 showing the stabilization of water-soluble vitamins in urine (Example 5)

In this case, (1) and (2) in FIG. 11 and (3) and (4) in FIG. 12 are cases in which the scales in the ordinates are different.

First, spot urine samples were collected from three healthy young adults. 9 mL of each of the spot urine samples and each 1 mL kind of acidic solution having a concentration of 1 mol/L were mixed, and the resultant samples were left still at 37° C. for 0, 3, and 7 days and frozen. Note that as for metaphosphoric acid, each urine sample was mixed with 1 mL of a 10% solution. Examples of a solution to be mixed were water, hydrochloric acid, ascorbic acid, oxalic acid, sulfosalicylic acid, tartaric acid, acetic acid, metaphosphoric acid, and citric acid. Under these conditions, vitamin concentrations of the frozen water-soluble vitamins in the urine samples were measured. More specifically, the vitamin concentrations of vitamin B1, vitamin B2, and vitamin B6 were measured by the HPLC method for thiamine, riboflavin, and vitamin B6 metabolite 4-pyridoxic acid, respectively. As for niacin, N1-methyl nicotinamide and N1-methyl-2-pyridone-5-carboxamide as the niacin metabolites were measured by the HPLC method, and their total amount was defined as a measurement result. In addition, as for pantothenic acid, folate, and biotin, the respective vitamin concentrations were measured by a microbiological determination. As for vitamin C, a total amount of ascorbic acid, dehydroascorbic acid, 2,3-ketogulonic acid was measured by the HPLC method.

Figure 13:
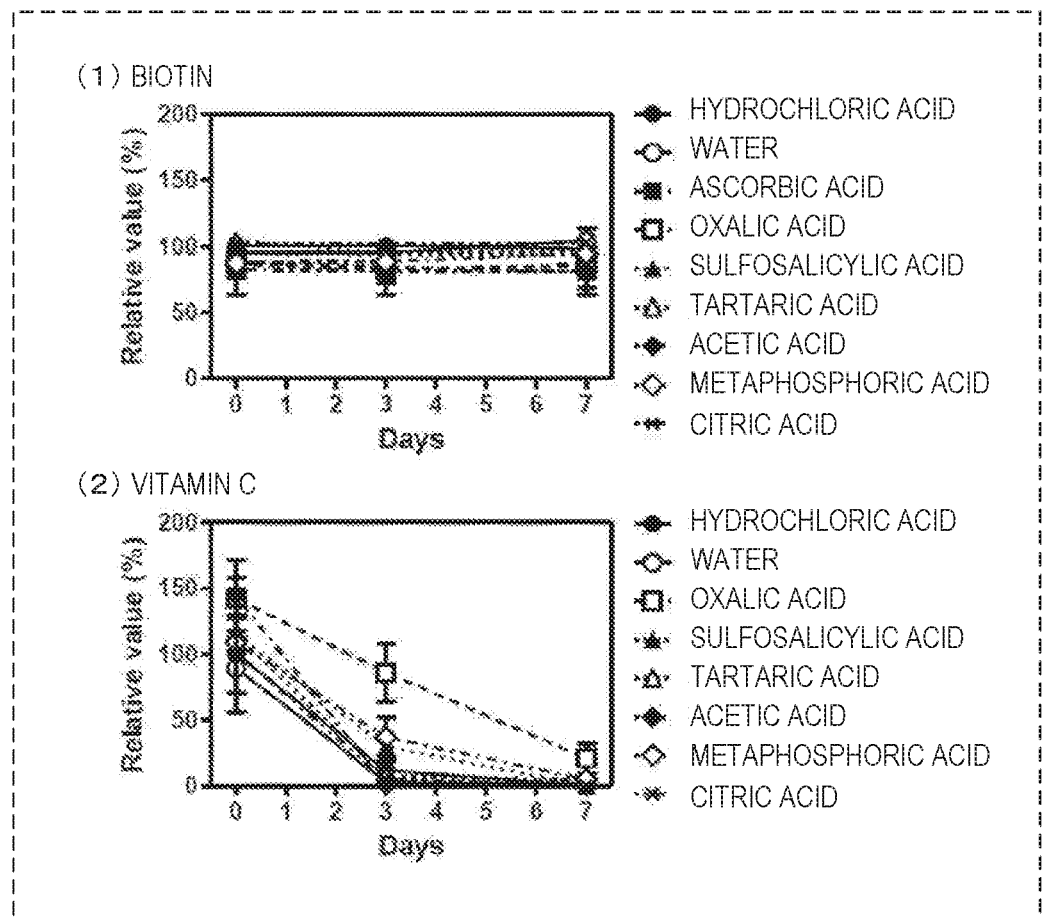
FIG. 13 shows graphs 3 showing the stabilization of water-soluble vitamins in urine (Example 5).

The graphs of the concentration changes in FIGS. 11 to 13 represent the relative values of the concentrations of the water-soluble vitamins in the urine samples treated with each kind of acidic solution using, as the references, the water-soluble vitamins in the urine samples treated with hydrochloric acid immediate after urine collection. Note that each value in each graph is indicated by a relative value average±standard deviation (n=3 but n=2 for vitamin C) with each chlorine acid treated sample immediately after urine collection.

As shown in the graphs of (1) and (2) in FIG. 11, as for vitamin B1, the urine thiamin concentrations were increased twice or more due to the storage of 3 or more days after the samples were treated with water and acetic acid. In other treatments, no large variations due to the 7-day storage were observed.

As shown in the graph of (3) in FIG. 11, as for vitamin B2, the urine riboflavin concentration was decreased to 56% due to the 7-day storage after the water treatment. On the other hand, the urine riboflavin concentrations were increased to about 1.8 times due to the 7-day storage after the treatments with hydrochloric acid, oxalic acid, and sulfosalicylic acid. In other treatments, no large variations due to the 7-day storage were observed.

As shown in the graph of (4) in FIG. 11, as for vitamin B6, no large variations due to the 7-day storage were observed in all the treatments.

As shown in the graph of (1) in FIG. 12, as for niacin, no large variations due to the 7-day storage were observed in all the treatments.

As shown in the graph of (2) in FIG. 12, as for pantothenic acid, the urine pantothenic acid concentration was decreased to 42% due to the 7-day storage after the treatment with sulfosalicylic acid. The urine pantothenic acid concentration was decreased to about 70% due to the oxalic acid treatment. In other treatments, no large variations due to the 7-day storage were observed.

As shown in the graphs of (3) and (4) in FIG. 12, as for folate, the urine folate concentrations were increased three or more times due to storage of 3 or more days after the water treatment. The urine folate concentrations due to the 7-day storage were stable with the treatments with ascorbic acid, oxalic acid, and tartaric acid. In other treatments, the urine folate concentrations were decreased to 50% to 70% due to the storage of 3 to 7 days.

As shown in the graph of (1) in FIG. 13, as for biotin, no large variations due to the 7-day storage were observed in all the treatments.

As shown in the graph of (2) in FIG. 13, as for vitamin C, no variation due to the 3-day storage was exhibited by only the oxalic acid treatment. In the remaining treatments, the total urine ascorbic acid concentrations was decreased to 30% or less due to the 3-day storage, and was decreased to almost 0% due to the 7-day storage. Metaphosphoric acid used to stabilize vitamin C in a biological sample could not stabilize vitamin C stably for 3 or more days. It may be assumed that 2,3-ketogulonic acid is further oxidized due to the storage at 37° C.

That is, as for the seven types of water-soluble vitamins except vitamin C, acids which exhibited the same stability as that of hydrochloric acid were tartaric acid and citric acid. Acetic acid cannot stably store vitamin B1, and ascorbic acid and metaphosphoric acid were poor in stability of vitamin B1. The stability of pantothenic acid by oxalic acid was a little inferior. Although sulfosalicylic acid could stably store pantothenic acid up to the 3rd day, no stability was observed in the 7-day storage. Only the oxalic acid treatment can stably store vitamin C for 3 days. However, the remaining acidic solutions could not stably store vitamin C for 3 or more days.

The summary of the influences of various kinds of acidic solutions on the concentrations of the water-soluble vitamins in the urine samples is shown in Table 3 below. In Table 3, the average value of the relative values falling with the range of 75% to 150% using, as the reference, the value of the 0-day hydrochloric acid treatment is evaluated as ○, the average value falling within the range of 50% to 75% or 150% to 200% using, as the reference, the value of the 0-day hydrochloric acid treatment is evaluated as Δ, and the average value falling within the range of less than 50% or 200% or more using, as the reference, the value of the 0-day hydrochloric acid treatment is evaluated as x.

TABLE 3

| Name of Solution | 0 Days | 3 Days | 7 Days | 0 Days | 3 Days | 7 Days | 0 Days | 3 Days | 7 Days | 0 Days | 3 Days | 7 Days |
|---|---|---|---|---|---|---|---|---|---|---|---|---|
| | Vitamin B1 | | | Vitamin B2 | | | Vitamin B6 | | | Niacin | | |
| Hydrochloric Acid | ○ | ○ | ○ | ○ | ○ | Δ | ○ | ○ | ○ | ○ | ○ | ○ |
| Water | ○ | X | X | ○ | ○ | Δ | ○ | ○ | ○ | ○ | ○ | ○ |
| Ascorbic Acid | Δ | ○ | ○ | ○ | ○ | ○ | ○ | ○ | ○ | ○ | ○ | ○ |
| Oxalic Acid | ○ | ○ | ○ | ○ | ○ | Δ | ○ | ○ | ○ | ○ | ○ | ○ |
| Sulfosalicylic Acid | ○ | ○ | ○ | ○ | ○ | Δ | ○ | ○ | ○ | ○ | ○ | ○ |

TABLE 3-continued

| Name of Solution | 0 Days | 3 Days | 7 Days | 0 Days | 3 Days | 7 Days | 0 Days | 3 Days | 7 Days | 0 Days | 3 Days | 7 Days |
|---|---|---|---|---|---|---|---|---|---|---|---|---|
| Tartaric Acid | ◯ | ◯ | ◯ | ◯ | ◯ | ◯ | ◯ | ◯ | ◯ | ◯ | ◯ | ◯ |
| Acetic Acid | ◯ | X | X | ◯ | ◯ | Δ | ◯ | ◯ | ◯ | ◯ | ◯ | ◯ |
| Metaphosphoric Acid | ◯ | Δ | Δ | ◯ | ◯ | ◯ | ◯ | ◯ | ◯ | ◯ | ◯ | ◯ |
| Citric Acid | ◯ | ◯ | ◯ | ◯ | ◯ | Δ | ◯ | ◯ | ◯ | ◯ | ◯ | ◯ |
|  | Pantothenic Acid | | | Folate | | | Biotin | | | Vitamin C | | |
| Hydrochloric Acid | ◯ | ◯ | Δ | ◯ | Δ | Δ | ◯ | ◯ | ◯ | ◯ | X | X |
| Water | ◯ | ◯ | ◯ | Δ | X | X | ◯ | ◯ | ◯ | ◯ | X | X |
| Ascorbic Acid | ◯ | ◯ | ◯ | ◯ | ◯ | ◯ | ◯ | ◯ | ◯ | — | — | — |
| Oxalic Acid | Δ | Δ | ◯ | ◯ | ◯ | ◯ | ◯ | ◯ | ◯ | ◯ | ◯ | X |
| Sulfosalicylic Acid | ◯ | ◯ | X | ◯ | ◯ | Δ | ◯ | ◯ | ◯ | ◯ | X | X |
| Tartaric Acid | ◯ | ◯ | ◯ | ◯ | ◯ | ◯ | ◯ | ◯ | ◯ | ◯ | X | X |
| Acetic Acid | ◯ | ◯ | ◯ | ◯ | Δ | Δ | ◯ | ◯ | ◯ | ◯ | X | X |
| Metaphosphoric Acid | ◯ | ◯ | ◯ | ◯ | Δ | Δ | ◯ | ◯ | ◯ | ◯ | X | X |
| Citric Acid | ◯ | ◯ | ◯ | ◯ | Δ | Δ | ◯ | ◯ | ◯ | ◯ | X | X |

From the above results, it was found that the acidic solutions usable as the stabilizers instead of hydrochloric acid were tartaric acid and citric acid. Although ascorbic acid is a little inferior in stability of vitamin B1, ascorbic acid is most superior in the stability of folate. It was found that it was very difficult to stably store vitamin C for 7 days even with the acidic solution treatment, but as for oxalic acid, the 3-day storage was possible.

Therefore, the acidic solutions usable as the stabilizers instead of hydrochloric acid are preferably tartaric acid, citric acid, and ascorbic acid, and it is possible to stabilize vitamin C by mixing oxalic acid.

Example 6

Normally, in a urine test, urine sugar (glucose: Glu) is said to become negative at room temperature. For example, according to "Effects of Lapse of Time and Temperature After Collection of Urine Specimens on Urinalysis", pages 789-797, Journal of the Japanese Association of Rural Medicine (Vol. 64, No. 5, January, 2016), the glycolytic action was observed in an *E. coli* added urine sample after 4 hours at room temperature of 25° C. to 26° C. or after 3 hours at 30° C. The pool urine sample containing 200 mg/dL of sugar was almost decomposed to zero after 24 hours. As for a *Proteus* added urine sample, *Proteus* tended to reduce the sugar after 7 hours at room temperature or after 6 hours at 30° C. in the pool urine sample containing 200 mg/dL of sugar.

This can generally represent data complementarily indicating that bacteria in each urine sample decompose glucose.

According to this example, the confirmation result of an experiment conducted to determine whether urine sugar is stabilized when an aqueous solution obtained by mixing citric acid and oxalic acid is added to a urine sample as a stabilizer, and the resultant sample is stored in room temperature will be described below.

As an experimental method, the glucose concentration (mg/dL) in a urine sample obtained by measuring urine sugar at the urine collection day (0th day) "without the stabilizer" was compared with that in a urine sample obtained by measuring urine sugar after 3 and 7 days "with the stabilizer".

The specimen "with the stabilizer" is obtained by mixing 8 mg of a urine sample with 2 mg of a stabilizer. In this manner, the specimen "with the stabilizer" is mixed with the stabilizer to dilute the urine sample. The specimen "without the stabilizer" was compared with the specimen "with the stabilizer" by multiplying the concentration of the specimen "without the stabilizer" by 0.8 to match the dilute concentration with the concentration of the specimen "with the stabilizer".

Table 4 below is the summary of the above experimental results. As shown in Table 4, the number of subjects is 10, that is, subject 1 to subject 10. The urine collection was performed three times for each subject, and the average value of the 3-time measurement values of each specimen was calculated.

Subject 1 was a 42-year old female, subject 2 was a 21-year old female, subject 3 was a 24-year old female, subject 4 was a 21-year old male, subject 5 was a 25-year old female, subject 6 was a 23-year old female, subject 7 was a 21-year old female, subject 8 was a 22-year old female, subject 9 was a 47-old male, and subject 10 was a 45-year old female.

The "0th day" in Table 4 indicates a numerical value obtained by multiplying the measurement value of the urine glucose concentration of the urine collection day "without the stabilizer" by 0.8. The "3rd day" indicates the measurement numerical value of the 3rd day after the urine collection "with the stabilizer". The "7th day" indicates the measurement numerical value of the 7th day after the urine collection "with the stabilizer".

The "after 3 days" indicates a value obtained by subtracting the measurement numerical value of the 3rd day after the urine collection "with the stabilizer" from a value obtained by multiplying the measurement numerical value of the urine glucose concentration on the urine collection day "without the stabilizer" by 0.8. The "after 7 days" indicates a value obtained by subtracting the measurement numerical value of the 7th day after the urine collection "with the stabilizer" from a value obtained by multiplying the measurement numerical value of the urine glucose concentration on the urine collection day "without the stabilizer" by 0.8. Therefore, the values of the "after 3 days" and the "after 7 days" indicate the decreasing degrees of the urine glucose concentrations. If each value is positive, the glucose concentration is decreased. If each value is negative, the glucose concentration is increased. Note that the values in Table 4 are properly rounded off

TABLE 4

| Subject | Glu (mg/dL) | | | | |
|---|---|---|---|---|---|
| | 0th Day | 3rd Day | 7th Day | After 3 Days | After 7 Days |
| Subject 1 | 6.40 | 5.67 | 6.33 | 0.73 | 0.07 |
| Subject 2 | 4.27 | 4.67 | 4.67 | −0.40 | −0.40 |
| Subject 3 | 7.20 | 8.00 | 9.00 | −0.80 | −1.80 |
| Subject 4 | 8.80 | 9.33 | 10.33 | −0.53 | −1.53 |
| Subject 5 | 11.47 | 11.33 | 10.67 | 0.14 | 0.80 |
| Subject 6 | 6.40 | 6.33 | 7.33 | 0.07 | −0.93 |
| Subject 7 | 6.93 | 7.00 | 7.33 | −0.07 | −0.40 |
| Subject 8 | 6.93 | 6.67 | 6.00 | 0.26 | 0.93 |
| Subject 9 | 6.13 | 6.67 | 6.00 | −0.54 | 0.13 |
| Subject 10 | 2.40 | 2.33 | 3.33 | 0.07 | −0.93 |

As shown in Table 4 above, the decreasing degree after 3 days of subject 1 was 0.73 mg/dL, and the decreasing degree after 7 days of subject 1 was −0.07 mg/dL. The decreasing degree after 3 days of subject 2 was −0.40 mg/dL, and the decreasing degree after 7 days of subject 2 was −0.40 mg/dL. The decreasing degree after 3 days of subject 3 was −0.80 mg/dL, and the decreasing degree after 7 days of subject 3 was −1.80 mg/dL. The decreasing degree after 3 days of subject 4 was −0.53 mg/dL, and the decreasing degree after 7 days of subject 4 was −1.53 mg/dL. The decreasing degree after 3 days of subject 5 was 0.14 mg/dL, and the decreasing degree after 7 days of subject 5 was 0.80 mg/dL. The decreasing degree after 3 days of subject 6 was 0.07 mg/dL, and the decreasing degree after 7 days of subject 6 was −0.93 mg/dL. The decreasing degree after 3 days of subject 7 was −0.07 mg/dL, and the decreasing degree after 7 days of subject 7 was −0.40 mg/dL. The decreasing degree after 3 days of subject 8 was 0.26 mg/dL, and the decreasing degree after 7 days of subject 8 was 0.93 mg/dL. The decreasing degree after 3 days of subject 9 was −0.54 mg/dL, and the decreasing degree after 7 days of subject 9 was 0.13 mg/dL. The decreasing degree after 3 days of subject 10 was 0.07 mg/dL, and the decreasing degree after 7 days of subject 10 was −0.93 mg/dL.

The average value of the changes in the decreasing degrees of the urine glucose concentrations of subjects 1 to 10 was −0.6, and the standard deviation of the changes was 1.0.

As described above, in the *E. coli* added urine sample, almost all the urine sugar was decomposed after 24 hours and became zero. As compared with this, the decrease in glucose concentration even 7 days after the urine collection was said to be small.

Therefore, by adding the aqueous solution obtained by mixing citric acid and oxalic acid as the stabilizer to the urine sample, the urine glucose concentration could be stabilized for at least 7 days after the urine collection.

Example 7

The confirmation result of the stabilization degrees of proteins, minerals, and vitamins, obtained by adding, to the urine samples, the aqueous solution obtained by mixing citric acid and oxalic acid as the urine stabilizer, will be described below. The stabilization degrees of sodium (Na), potassium (K), phosphorus (P), calcium (Ca), magnesium (Mg), and molybdenum (Mo) as the minerals were confirmed. The stabilization degrees of vitamin B1, vitamin B2, vitamin B6, niacin, pantothenic acid, folate, and biotin as the vitamins were confirmed. As the experimental method, samples measured on the urine collection day (0th day), 3rd day, after one week (7th day), 10th day, and after two weeks (14th day) were compared with each other. The urine samples added with stabilizers were stored at room temperature (20° C.). The number of subjects was four. In each measurement, urine collection was performed twice for each subject. The average value of the measurement values was calculated, and the average value of the four subjects in each measurement was calculated. The results are shown in Table 5 below.

TABLE 5

| Average Decrease Rate (%) | Protein (mg/dL) | Na (mg/L) | K (mg/L) | P (mg/L) | Ca (mg/L) | Mg (mg/L) | Mo (μg/l) |
|---|---|---|---|---|---|---|---|
| 0th Day | 0 | 0 | 0 | 0 | 0 | 0 | 0 |
| 3rd Day | −0.2 | 0.1 | −4.9 | 5.7 | 1.3 | −3.4 | −535.2 |
| 7th Day | −1.7 | 0.4 | 1.8 | 1.2 | −1.2 | 3.2 | −155.7 |
| 10th Day | −3.2 | −1.9 | 0.2 | 7.5 | −2.0 | 7.3 | −556.4 |
| 14th Day | 0.8 | 0.1 | 1.4 | 8.8 | −0.9 | −1.3 | −440.5 |

| Average Decrease Rate (%) | Vitamin B1 (ng/mL) | Vitamin B2 (ng/mL) | Vitamin B6 (ng/mL) | Niacin (ng/mL) | Pantothenic Acid (ng/mL) | Folate (ng/mL) | Biotin (ng/mL) |
|---|---|---|---|---|---|---|---|
| 0th Day | 0 | 0 | 0 | 0 | 0 | 0 | 0 |
| 3rd Day | 12.8 | 12.3 | 5.8 | 6.0 | −11.7 | −139.6 | −2.8 |
| 7th Day | 16.6 | 6.6 | 13.0 | −1.7 | 11.1 | −147.0 | −28.7 |
| 10th Day | 14.0 | −4.0 | 15.7 | 1.6 | 5.2 | −197.2 | −45.7 |
| 14th Day | −16.8 | −30.7 | 25.1 | 2.6 | 14.2 | −267.6 | −61.8 |

The following facts were confirmed from Table 5. That is, by adding, to the urine samples, the aqueous solution obtained by mixing citric acid and oxalic acid as the urine stabilizer, stability of the urine protein concentrations was confirmed for 14 days throughout the measurements. In addition, by adding, to the urine samples, the aqueous solution obtained by mixing citric acid and oxalic acid as the urine stabilizer, stability of the concentrations of the urine minerals as sodium (Na), potassium (K), phosphorus (P), calcium (Ca), and magnesium (Mg) was confirmed for 14 days throughout the measurements. In this case, molybdenum (Mo) has a large increase amount (since the value is negative, the amount is an increase) from the 3rd-day measurement. This is because the molybdenum concentrations in the urine samples are on the order of μg/mL which is a small amount smaller than other minerals on the three orders of magnitude, and the measurements may be caused by the measurement resolution.

On the other hand, by adding, to the urine samples, the aqueous solution obtained by mixing citric acid and oxalic acid as the urine stabilizer, stability of the concentrations of urine vitamins such as vitamin B1, vitamin B2, vitamin B6, niacin, pantothenic acid, and biotin was confirmed up to the 10th day. It was confirmed that folate was increased from the 3rd-day measurement and became stable without greatly changing the increase amount until the 10th day.

Example 8

The aqueous solution obtained by mixing citric acid and oxalic acid as the urine stabilizer was added to urine samples, and the samples were frozen and stored for several days. After that, the samples were defrosted, and the confirmation results of the stabilization degrees of proteins, minerals, and vitamins will be described below. The concentrations of the urine minerals as sodium (Na), potassium (K), phosphorus (P), calcium (Ca), magnesium (Mg), and molybdenum (Mo) were confirmed. The concentrations of the urine vitamins as vitamin B1, vitamin B2, vitamin B6, niacin, pantothenic acid, folate, and biotin were confirmed. As an experimental method, samples measured on the urine collection day (0th day), samples defrosted after the samples were frozen for 7 days, and samples obtained by defrosted after the samples were frozen for 20 days were compared with each other. Frozen storage was performed in a −10° C. freezer, and defrosting was performed by natural defrost at room temperature (20° C.). The number of subjects was four, and the average value of the four subjects in each measurement was calculated. The results are shown in Table 6 below.

TABLE 6

| Average Decrease Rate (%) | Protein (mg/dL) | Na (mg/L) | K (mg/L) | P (mg/L) | Ca (mg/L) | Mg (mg/L) | Mo (µg/l) |
|---|---|---|---|---|---|---|---|
| 0th Day | 0 | 0 | 0 | 0 | 0 | 0 | 0 |
| 7-day Freezing | −3 | 3 | 3 | 1 | 0 | 3 | −66 |
| 20-day Freezing | −12 | 6 | 11 | 5 | 1 | 2 | −474 |

| Average Decrease Rate (%) | Vitamin B1 (ng/mL) | Vitamin B2 (ng/mL) | Vitamin B6 (ng/mL) | Niacin (ng/mL) | Pantothenic Acid (ng/mL) | Folate (ng/mL) | Biotin (ng/mL) |
|---|---|---|---|---|---|---|---|
| 0th Day | 0 | 0 | 0 | 0 | 0 | 0 | 0 |
| 7-day Freezing | 25 | 9 | −3 | −1 | 4 | −71 | −25 |
| 20-day Freezing | 19 | −11 | 22 | 7 | 8 | −197 | −44 |

The following facts were confirmed from Table 6. That is, by adding, to the urine samples, the aqueous solution obtained by mixing citric acid and oxalic acid as the urine stabilizer, stability of the urine protein concentrations of the samples obtained by defrosting the samples after the samples were frozen for 7 days and the samples obtained by defrosting the samples after the samples were frozen for 20 days was confirmed. In addition, by adding, to the urine samples, the aqueous solution obtained by mixing citric acid and oxalic acid as the urine stabilizer, stability of the concentrations of the urine minerals as sodium (Na), potassium (K), phosphorus (P), calcium (Ca), and magnesium (Mg) of the samples obtained by defrosting the samples after the samples were frozen for 7 days and the samples obtained by defrosting the samples after the samples were frozen for 20 days was confirmed. In this case, molybdenum (Mo) has a large increase amount (since the value is negative, the amount is an increase) from the samples obtained by defrosting the samples after the samples were frozen for 7 days measurement. This is because the molybdenum concentrations in the urine samples are on the order of µg/mL which is a small amount smaller than other minerals on the three orders of magnitude, and the measurements may be caused by the measurement resolution.

On the other hand, by adding, to the urine samples, the aqueous solution obtained by mixing citric acid and oxalic acid as the urine stabilizer, stability of the concentrations of urine vitamins such as vitamin B1, vitamin B2, vitamin B6, niacin, pantothenic acid, and biotin of the samples obtained by defrosting the samples after the samples were frozen for 7 days and the samples obtained by defrosting the samples after the samples were frozen for 20 days was confirmed.

INDUSTRIAL APPLICABILITY

The present invention is useful to a urine testing apparatus.

The invention claimed is:
1. A urine testing apparatus for testing urine comprising a first urine collection storage container, said urine testing apparatus further comprising, as a urine stabilizer, at least one selected from the group consisting of:
   an agent obtained by drying or freeze-drying a mixture of an aqueous citric acid solution and an aqueous oxalic acid solution;
   an inner wall coated with a mixture of an aqueous citric acid solution and an aqueous oxalic acid solution;
   a second container containing a mixture of an aqueous citric acid solution and an aqueous oxalic acid solution; and
   a medium impregnated with a mixture of an aqueous citric acid solution and an aqueous oxalic acid solution.
2. A urine testing method comprising:
   adding, to collected urine as a urine stabilizer, at least one selected from the group consisting of
   1) a mixture of an aqueous citric acid solution and an aqueous oxalic acid solution;
   2) an agent obtained by drying or freeze-drying a mixture of an aqueous citric acid solution and an aqueous oxalic acid solution; and
   3) a medium impregnated with a mixture of an aqueous citric acid solution and an aqueous oxalic acid solution stabilizer; and testing the collected urine within 7 days after adding one of the aqueous solution, the agent, and the medium.

3. The urine testing method according to claim 2, wherein the testing comprises:
measuring a urine vitamin concentration of at least one selected from the group consisting of vitamin B1, vitamin B2, vitamin B6, niacin, pantothenic acid, folate, and biotin, and
measuring a urine mineral concentration of at least one selected from the group consisting of sodium, calcium, potassium, phosphorus, and magnesium.

4. The urine testing method according to claim 2, wherein by adding the stabilizer, the urine vitamin concentration is stabilized under a condition of 37° C. for at least 7 days after urine collection.

5. A urine stabilizer for stabilizing at least one component of collected urine comprising at least one selected from the group consisting of:
a mixture of an aqueous citric acid solution and an aqueous oxalic acid solution,
an agent obtained by drying or freeze-drying a mixture of an aqueous citric acid solution and an aqueous oxalic acid solution, and
a medium impregnated with a mixture of an aqueous citric acid solution and an aqueous oxalic acid solution.

6. The urine testing method according to claim 2, wherein the testing comprises:
measuring a urine vitamin concentration of at least one selected from the group consisting of vitamin B1, vitamin B2, vitamin B6, niacin, pantothenic acid, folate, and biotin.

7. The urine testing method according to claim 2, wherein the testing comprises:
measuring a urine mineral concentration of at least one selected from the group consisting of sodium, calcium, potassium, phosphorus, and magnesium.

8. The urine testing apparatus according to claim 1, comprising the agent.

9. The urine testing apparatus according to claim 1, comprising the inner wall.

10. The urine testing apparatus according to claim 1, comprising the second container.

11. The urine testing apparatus according to claim 1, comprising the medium.

12. The urine testing apparatus according to claim 1, wherein the mixture further comprises tartaric acid, ascorbic acid, or tartaric acid and ascorbic acid.

13. The urine testing method according to claim 2, comprising adding the mixture to the collected urine.

14. The urine testing method according to claim 2, comprising adding the agent to the collected urine.

15. The urine testing method according to claim 2, comprising adding the medium to the collected urine.

16. The urine testing method according to claim 2, wherein the mixture further comprises tartaric acid, ascorbic acid, or tartaric acid and ascorbic acid.

17. A urine stabilizer according to claim 5, comprising the mixture.

18. A urine stabilizer according to claim 5, comprising the agent.

19. A urine stabilizer according to claim 5, comprising the medium.

20. The urine stabilizer according to claim 5, wherein the mixture further comprises tartaric acid, ascorbic acid, or tartaric acid and ascorbic acid.

* * * * *